United States Patent
Hofer-Kraner et al.

(10) Patent No.: US 9,610,198 B2
(45) Date of Patent: Apr. 4, 2017

(54) PROTECTION DEVICE FOR A WELDER

(71) Applicant: OPTREL AG, Wattwil (CH)

(72) Inventors: Ramon Hofer-Kraner, Herisau (CH); Leo Keller, Rueti (CH)

(73) Assignee: OPTREL AG, Wattwil (CH)

(*) Notice: Subject to any disclaimer, the term of this patent is extended or adjusted under 35 U.S.C. 154(b) by 0 days.

(21) Appl. No.: 14/859,418

(22) Filed: Sep. 21, 2015

(65) Prior Publication Data

US 2016/0081856 A1 Mar. 24, 2016

(30) Foreign Application Priority Data

Sep. 24, 2014 (CH) ...................................... 1447/14

(51) Int. Cl.
*A61F 9/06* (2006.01)

(52) U.S. Cl.
CPC .............. *A61F 9/061* (2013.01); *A61F 9/062* (2013.01); *A61F 9/064* (2013.01); *A61F 9/065* (2013.01); *A61F 9/067* (2013.01); *G02F 2201/44* (2013.01)

(58) Field of Classification Search
CPC .. A61F 9/06; A61F 9/029; A61F 9/045; A61F 9/061; A61F 9/064; A61F 9/067; A42B 3/18; A42B 3/185; A42B 3/22; A42B 3/222; A42B 3/225; A61B 19/04; A61B 42/00
USPC ................................... 2/8.2–8.4, 9
See application file for complete search history.

(56) References Cited

U.S. PATENT DOCUMENTS

| | | | | |
|---|---|---|---|---|
| 2,761,046 A | * | 8/1956 | Herrick | A61F 9/061 2/8.3 |
| 4,076,373 A | * | 2/1978 | Moretti | A61F 9/025 2/434 |
| 4,686,711 A | * | 8/1987 | Budmiger | A61F 9/061 2/8.3 |
| 5,764,330 A | * | 6/1998 | Simioni | G02C 5/2209 16/228 |
| 6,097,451 A | * | 8/2000 | Palmer | A61F 9/067 349/14 |
| 2004/0179149 A1 | | 9/2004 | Wang-Lee | |

(Continued)

FOREIGN PATENT DOCUMENTS

EP      0302212 A1    6/1988
EP      0 302 212 A1    2/1989

OTHER PUBLICATIONS

Extended European Search Report dated Feb. 1, 2016 issued in corresponding EP patent application No. 15186401.4.

(Continued)

*Primary Examiner* — Katherine Moran
(74) *Attorney, Agent, or Firm* — Posz Law Group, PLC (57) ABSTRACT

A welder protection device comprising a shell and a transparent front cover for protection of a wearer of the welder protection device, and an auto-darkening optical filter. The welder protection device further comprises a retracting mechanism arranged to move the optical filter optical filter from an active position to a retracted position and vice versa. In the active position, the optical filter lies inside the welder protection device and in the wearer's field of view, and in the retracted position the optical filter lies inside the welder protection device and outside the wearer's field of view.

19 Claims, 6 Drawing Sheets

(56) References Cited

U.S. PATENT DOCUMENTS

| | | | | |
|---|---|---|---|---|
| 2010/0287676 A1* | 11/2010 | Seo | ................ | A61F 9/064 2/8.2 |
| 2011/0179541 A1* | 7/2011 | Wright | ................ | A61F 9/064 2/12 |
| 2014/0013479 A1* | 1/2014 | Magnusson | ............ | A61F 9/067 2/8.7 |
| 2015/0033431 A1* | 2/2015 | Hofer Kraner | ......... | A61F 9/067 2/8.8 |

OTHER PUBLICATIONS

European Search Report issued on Jan. 16, 2015 in the corresponding CH application No. 14472014. (Partial translation attached).

* cited by examiner

PROTECTION DEVICE FOR A WELDER

CROSS REFERENCE TO RELATED APPLICATION

This application is based on and incorporates herein by reference Swiss Patent Application No. 01447/14 filed on Sep. 24, 2014.

The invention relates to the field of protection devices for welders comprising anti dazzle filters or auto-darkening filters for protection of the welder's eyes, and in particular to a protection device for a welder as described in the preamble of the independent claim.

Anti-dazzle filters used in welding protection applications, e.g. in welding helmets or welding masks, use optical detection means to detect the presence of a welding arc and to trigger a darkening of the filter, e.g. a liquid crystal (LC) device, which is automatically switched to a darkening state with a required working shade level.

Welding protection helmets typically comprise injection molded, non-transparent face shields that are attached to a stiff headgear. The face shield usually has a rectangular window incorporating a passive or active welding protection filter. The window can be covered by a protective front cover, which usually is called a "lens". In the case of an active protection device, the shield holds a cartridge type auto-darkening opto-electronic shutter insert that is positioned relatively far from the eye. The user's field-of-view is restricted due to this distance, resulting in a tunnel-like view of the welding area. Due to the weight of the welding filter and its distance from the user's spinal column, an imbalance results which causes neck pain in the short term and neck injury in the long term. This situation is aggravated when purifying air-powered respirators (PAPR) are worn. PAPR protective devices use tight face seals that are attached to the welding helmet and enfold the neck closely, forming a tight seal against the surrounding atmosphere. Such devices cannot be taken off after each single weld because of the tight face-seal and the polluted surrounding atmosphere.

Patent Application US 2014/0013479 A1 discloses a welding helmet in which two optically active side filters are integrated into the welding helmet at an angle to the plane of a central main welding filter. They provide a limited view to the side, but do not provide for a large unobstructed viewing area.

Patent Application EP 0 302 212 A1 discloses a swivel-guided passive visor that makes a forward-backward-upward movement. The application is directed to motorcyclist helmets and describes the combined rotating and translating mechanism in detail. The visor can be retracted into the inside or over the outside of a helmet.

U.S. Pat. No. 8,555,424 B2 discloses another guiding mechanism that moves a passive visor, typically that of a sports helmet, into a desired position.

US Patent application 20080060102 A1 shows a re-configurable welding helmet assembly. It describes different welding helmet configurations such as a detachable front module that contains different inserts, it explains how the welding filter can be mounted as interior lens, or, as flip-up device, and, it describes the adjustable headgear in order to adapt the lens to the eye position within the limits of the concept. The application does not refer to the limits of welding helmet concepts and does not address either the wide field-of-view or the issue of attenuation in the clear state of the filter.

The company Servore, Korea, offers a series of protective helmets under the brand name "AutoLift" to be used for both welding and grinding. It comprises a face protector and an outer swivel mechanism with which an auto-darkening filter mounted on the outside of the face protector can be rotated to lie within or outside of the user's line of sight (SparxLift Welding Helmet Sales Brochure). The helmet has only a small field of view when the filter lies in the user's line of sight.

It is therefore an object of the invention to create a protection device for a welder of the type mentioned initially, which overcomes the disadvantages mentioned above.

These objects are achieved by a welder protection device according to the claims.

The welder protection device comprises a shell and a transparent front cover for protection of a wearer of the welder protection device, and an auto-darkening optical filter. The welder protection device further comprises a retracting mechanism arranged to move the optical filter from an active position to a retracted position and vice versa, wherein in the active position the optical filter lies inside the welder protection device and in wearer's field of view, and in the retracted position the optical filter lies inside the welder protection device and outside the wearer's field of view.

The welder protection device consequently allows for a close-to-the-eye configuration of the optical filter. This results in a much larger field-of-view during welding when compared to current products. When the optical filter is retracted, the ultra-large front cover (lens) provides for a large field-of-view of, for example, almost 180° laterally. It can incorporate functional elements such as partial UV protection means. The optically active welding filter can be a known type of filter complying with current welding standards. It can be part of a filter cassette comprising e.g. the optically active filter element itself and additional elements such as a battery, sensors and circuitry for controlling the filter. Alternatively, the active filter can be implemented in a housing separate from such additional elements. It can be placed, in the active position, directly behind the highly transparent front cover. The optical filter can swivel into the upper or the side part of the welding helmet. In this way, a truly unattenuated view of the workplace environment is achieved. The clear protective front cover provides the comfort of having a truly undisturbed view of the entire working area. It can remain in place for grinding, brazing and cutting operations as well as under difficult working conditions such as with PAPR respiratory protection equipment.

In an embodiment, the wearer's field of view is determined by an opening in the shell, the shell being opaque (or intransparent) and the opening being covered by the transparent front cover, and when the optical filter is in the active position, the optical filter and a filter carrying element cover the opening.

As a result, when the optical filter is in the active position, the optical filter and the filter carrying element block incident light that reaches the opening from passing to the inside of the welder protection device.

In an embodiment, when the optical filter is in the retracted position, the optical filter is arranged adjacent to the opening, not covering or not substantially covering the opening.

As a result, when the optical filter is in the retracted position, the optical filter and the filter carrying element do not block incident light that reaches the opening from passing to the inside of the welder protection device, giving the wearer a view limited only by the size of the opening.

The optical filter, as it is retracted or moved back to the active position, moves within the welder protection device and in particular within or behind a shell and a front cover of the device.

The optical filter typically comprises one or more optically active elements and is configured to automatically switch from a transparent (or clear) state to a blocking (or darkened) state when a welding arc is detected. Detection can be effected e.g. by means of one of or a combination of means such as electrical, optical, magnetic or remote signals, including pre-trigger-signals generated by welding equipment. In the clear state, transmittance can be larger than 30%.

In an embodiment, the optical filter comprises a concave cutout for accommodating a wearer's nose.

In other words, in this embodiment the optical filter is not of a rectangular shape as is common. It can therefore be brought into closer proximity to the wearer's eyes, allowing for a larger field-of-view than a rectangular optical filter having the same size in the vertical direction. When the protection device is worn by a wearer and the optical filter is in the active position, the cutout provides room for the wearer's nose. It can rest on the bridge of the wearer's nose.

In an embodiment, in the active position, when the welder protecting device is worn by a wearer, the optical filter is distanced from the wearer's eyes by 20 mm to 40 mm.

In an embodiment, the welder protection device comprises a detection unit configured to automatically activate the retracting mechanism to move the optical filter from the active position to the retracted position when a welding operation has stopped.

The retracting mechanism can comprise an actuator element such as an electric motor or a magnet that drives the retracting mechanism or releases a catch which then allows the retracting mechanism to be moved by a spring.

In an embodiment, the retracting mechanism is manually brought into the active position against the tension of spring element, with a catch holding the retracting mechanism in the active position. For moving the retracting mechanism back to the retracted position, the catch can be released manually, e.g. by the wearer pressing a release element. In another embodiment, the catch is released automatically, for example electromechanically, for example when the detection unit detects an end of a welding operation. In both cases, i.e. manual or automatic release, the release element can move the catch or a holding element that holds the catch, thereby releasing the catch.

In an embodiment, the detection unit operates in a manner known from auto-darkening welding filters, which detect the presence of a welding activity, e.g. with an optical or electrical sensor, or receive a signal that indicates that a welding operation takes place. The detection unit detects the absence of a welding activity.

In an embodiment, the detection unit is configured to automatically activate the retracting mechanism in the absence of a welding activity only after the presence of a welding arc has been detected. The detection unit can be configured to wait a predetermined time interval after the absence of a welding activity has been detected, before it activates the retracting mechanism. If during this time interval a further welding activity is detected, the detection unit again waits until this further welding activity has ended. The predetermined time interval can be stored in the detection unit or set by a user.

In an embodiment, the welder protecting device comprises a manual switch configured to activate the retracting mechanism to move the optical filter from the active position to the retracted position or vice versa. In other embodiments, the retracting mechanism is mechanically operated, e.g. by a lever that is accessible to the wearer of the welder protecting device.

In an embodiment, the retracting mechanism moves the optical filter from the active to the retracted position along an arcuate path.

In an embodiment, the retracting mechanism moves separate sections of the optical filter from the active to the retracted position each along different translational and/or rotational trajectories.

This allows for the optical filter to comprise separate sections that can be moved independently. A first section can be moved along a first path involving a translation and/or a rotation of the first section. A second section can be moved along a second path involving a translation and/or a rotation of the second section. The second and first path are different from each other, but typically are mirror-symmetric to each other.

In an embodiment, the front cover comprises a laminate comprising a stack of superimposed sheets each sheet adhering to an underlying sheet, wherein each sheet can be peeled off its underlying sheet.

The sheets can be peeled off one after the other when the outermost sheet is damaged by staining, sparks, welding spatter, fumes etc, which often limits the sight of the worker or creates an intense diffusion of light. By peeling off one of the sheets the optically clear surface of the protective lens can be restored several times (according to the number of stacked sheets) before the protective lens has to be replaced.

The front cover can be formed as punched or injection molded structure that incorporates partial UV absorption means fulfilling current welding standards together with the welding filter.

The welding filter itself can be built as slim-form-active-shutter element that has only a basic welding filter configuration such as at least one liquid crystal (LC) shutter element comprising UV/IR-reflecting/absorbing characteristics together with the front cover lens according to global welding standards such as EN 379/169, ANSI Z87.1, CSA Z94.3-07, AS/NZS 1338.1. If only one liquid crystal shutter element is used, the transmittance of the shutter, approximately 30%, is sufficient to recognize minute details in the clear state of the welding filter under difficult lighting conditions and the filter does therefore not have to be retracted. However, if darker shade numbers are required due to higher welding currents, more than one liquid crystal shutter elements are usually used in a series configuration, light passing through one shutter element after the other. Then, swiveling the welding filter out of the field-of-view of the welder provides an unattenuated view through the protective front cover lens.

The welder protection device can also be used in other context than with welding, where protection against strong light emissions is required. Such a context is, for example, work in electrical installations, where fault arcs can occur. So in a more general sense, the invention also can relate to a protecting device not necessarily related to welding or use by a welder.

Further embodiments are evident from the dependent patent claims.

The subject matter of the invention will be explained in more detail in the following text with reference to exemplary embodiments which are illustrated in the attached drawings, which show in FIGS. 1 and 2 different views of a welder protecting device.

In principle, identical parts are provided with the same reference symbols in the figures.

Figure 1:
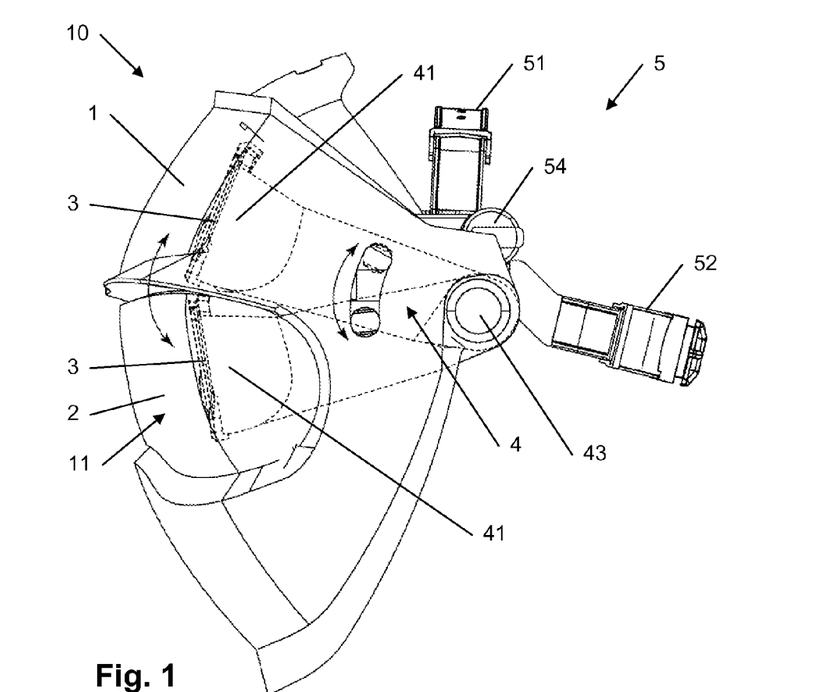
Figure 2:
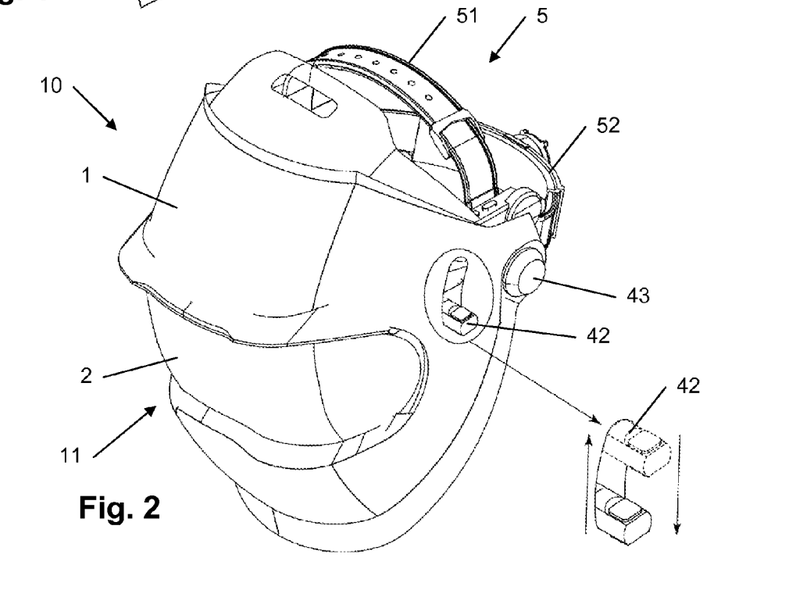

FIGS. 1 and 2 show different views of a welder protecting device 10. The welder protecting device 10 comprises a shell 1 held by a support 5. The shell 1 covers and protects the remaining elements of the welder protecting device 10 from sparks and spatter from grinding. The shell 1 comprises a viewing opening 11 covered by a transparent front cover 2, often also called lens. An optical filter 3 is moved by a retracting mechanism 4 and carried by a filter carrying element 41. The optical filter 3 can be moved from an active position behind the opening 11 and front cover 2 to a retracted position which allows a free view through the opening 11 and front cover 2. Both positions are indicated in FIG. 1 by dashed lines. The motion of the retracting mechanism 4 is swiveling motion around a hinge 43. The retracting mechanism 4 can be operated by a lever 42 attached to the filter carrying element 41 and extending outwards through a slot in the shell 1.

Figures 3, 4, 5:
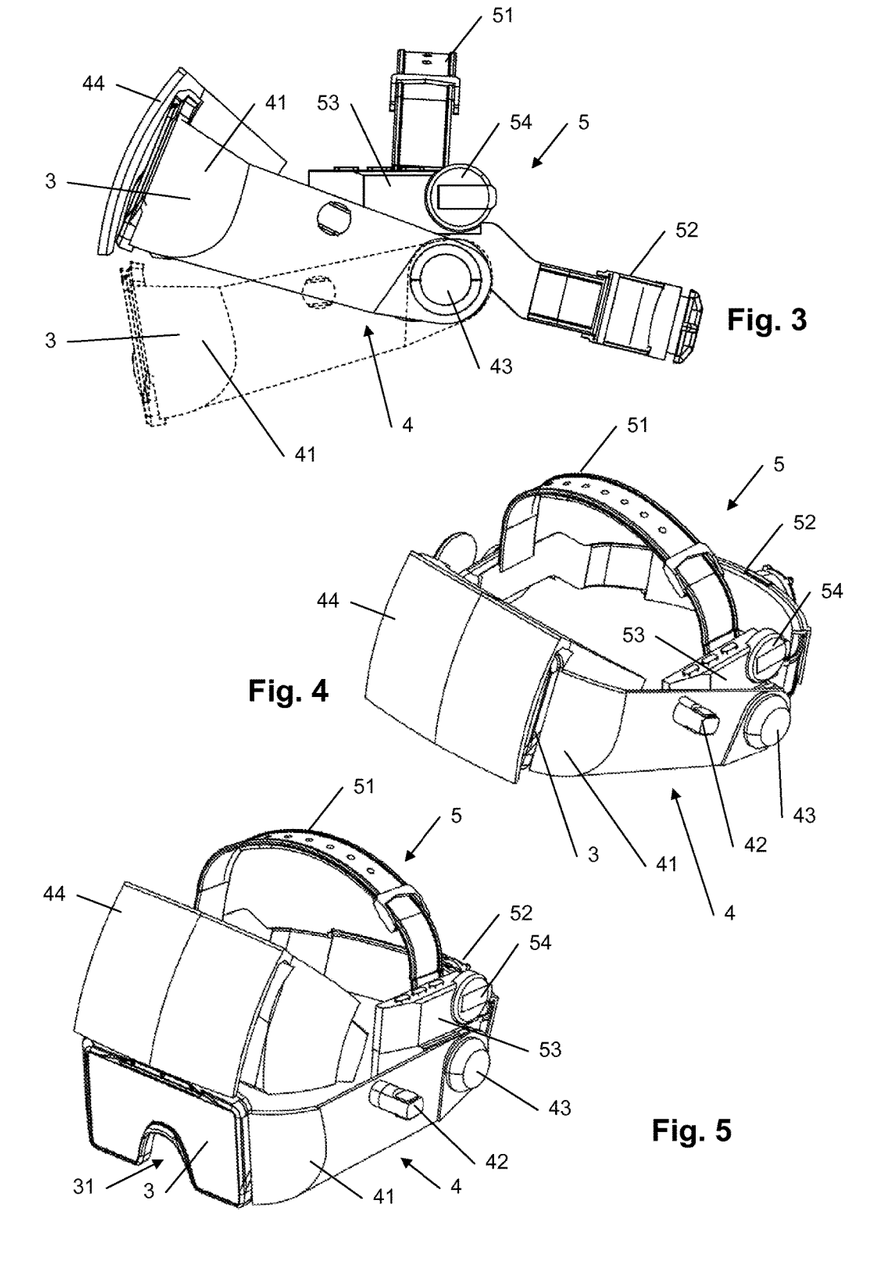
FIG. 3 a support and a filter carrying element in different positions.
FIG. 4 the support with the filter carrying element in a retracted position.
FIG. 5 the support with the filter carrying element in an active position.
Figure 6A:
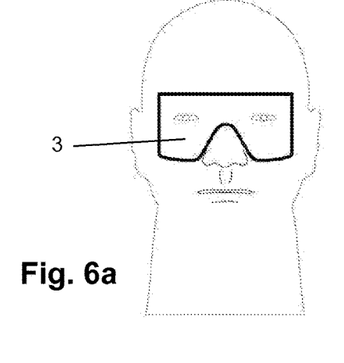
FIG. 6*a-d* an optical filter retracted by moving upwards.
Figure 6B:
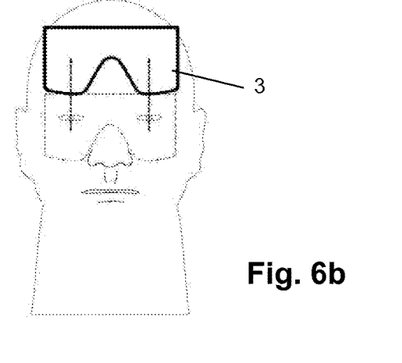
Figures 6C, 6D:
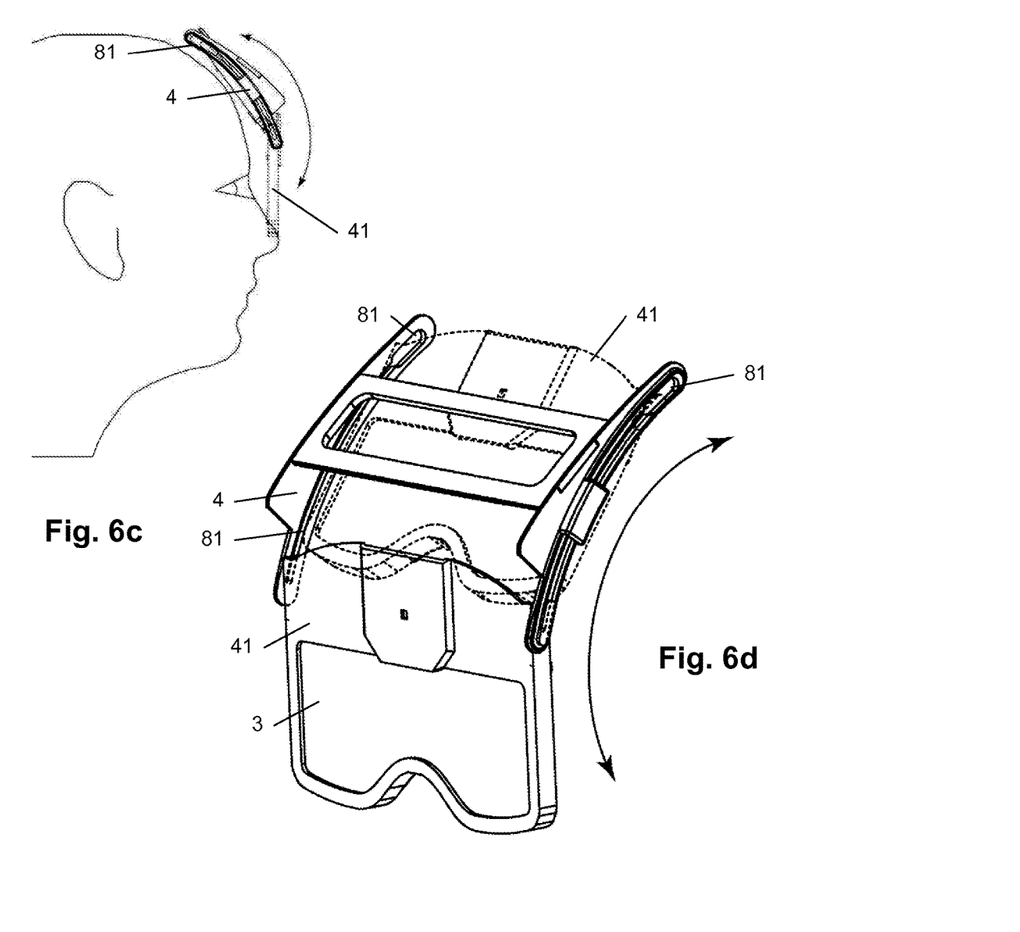

FIG. 3 shows details of the support 5 and further elements relevant to the movement of the optical filter 3. The support 5 comprises a upper strap 51 and a rear strap 52 attached to a connecting element 53. The connecting element 53 serves as a mechanical connection but can also comprise a first controller with electronic components and buttons for controlling the transmittance of the optical filter 3. The connecting element 53 can also comprise a second controller with electronic components for sensing and/or activating a movement of the filter carrying element 41. A switch or dial 54 can be configured to interact with one or both of the controllers.

The filter carrying element 41 is drawn with solid lines in an upper, retracted position, and with dashed lines in a lower, active position. The filter carrying element 41 holds the optical filter 3 and is rotatable about a hinge 43. The hinge 43 is attached to the shell 1 and/or to the support 5.

A bay 44 is attached to the shell 1 and/or to the support 5. The bay 44 can serve as a receptacle or to receive or park the optical filter 3 when it is in the retracted or parked position. The bay 44 can hold and protect the optical filter 3 in the parked position. The bay 44 can comprise guide elements that guide the movement of the optical filter 3 and/or the filter carrying element 41.

FIG. 4 shows the support 5 with the filter carrying element 41 in a retracted position, with the optical filter 3 in the bay 44.

FIG. 5 shows the support 5 with the filter carrying element 41 in an active position, with the optical filter 3 outside the bay 44. The optical filter 3 comprises a nose cutout 31 in its lower edge, corresponding to the location of the wearer's nose.

FIGS. 6*a-d* show an optical filter 3 that can be retracted by moving the optical filter 3 upwards. This upward motion can be effected by rotating the optical filter 3 upwards along an arcuate path, as in the embodiments of FIGS. 3 to 5, or by sliding the optical filter 3 upwards along a linear or arcuate path. The retracting mechanism 4 can comprise linear or arcuate (as in FIGS. 6*c* and 6*d*) slots 81 guiding the filter carrying element 41 along the arcuate path.

The remaining figures show variants of the welder protecting device in which the optical filter 3 comprises two independently movable sections, in particular halves.

FIG. 7*a-h* show an optical filter retracted by rotating the separate sections 3*a*, 3*b* of the optical filter 3 upwards. The axes of rotation of each of the sections 3*a*, 3*b* lie in the region of the middle of a top edge of the optical filter 3. The axes are at least approximately perpendicular to a plane in which the optical filter 3 extends. This plane is parallel to a front surface and a back surface of the optical filter 3 through which light passes or is attenuated by the optical filter 3. The separate sections 3*a*, 3*b* can be rotated by an actuator element or drive mechanism 82 comprising e.g, an electromechanical actuator or a spring actuator or a combination thereof.

Figure 7A:
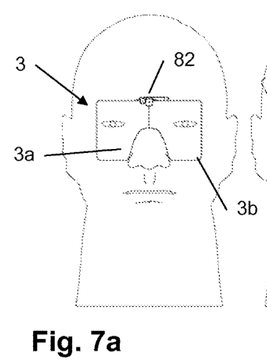
FIG. 7*a-h* an optical filter retracted by rotating upwards.
Figures 7B, 7C:
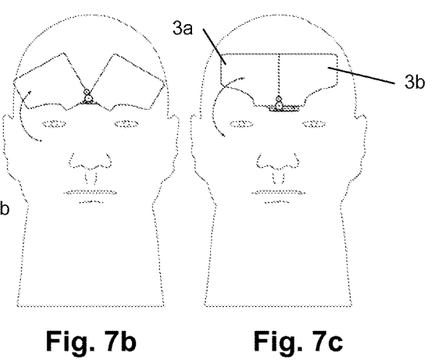
Figure 7D:
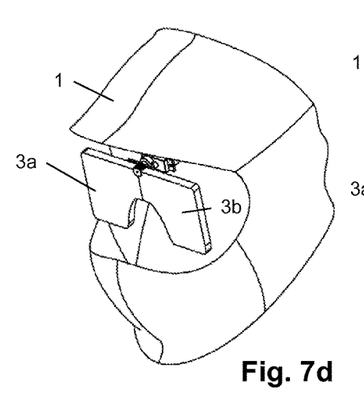
Figure 7E:
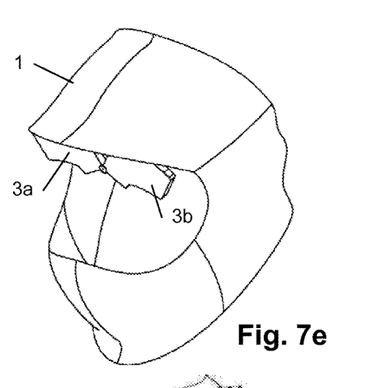
Figure 7F:
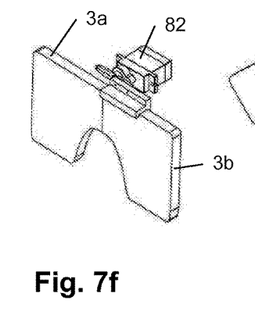
Figure 7G:
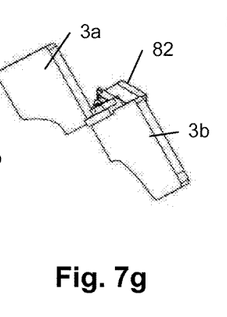
Figure 7H:
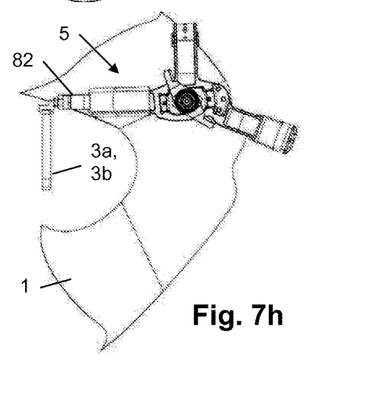

FIG. 7*a* shows the sections in an active position. FIG. 7*b* shows the separate sections 3*a*, 3*b* in a first retracted position in which the sections are partially retracted but the wearer's field-of-view is hardly obstructed since nose cutout sections of the separate sections 3*a*, 3*b* lie in a region in front of the wearer's eyes. FIG. 7*c* shows the separate sections 3*a*, 3*b* in a second retracted position, in which the separate sections 3*a*, 3*b* are fully retracted. FIGS. 7*d* and 7*e* show the arrangement of the sections 3*a*, 3*b* in relation to the shell 1; for the sake of illustration the other elements are not drawn. FIGS. 7*f* and 7*g* show just the separate sections 3*a*, 3*b* and the drive mechanism 82 in different positions, and FIG. 7*h* shows the separate sections 3*a*, 3*b* and drive mechanism 82 attached to the support 5.

Figures 8A, 9:
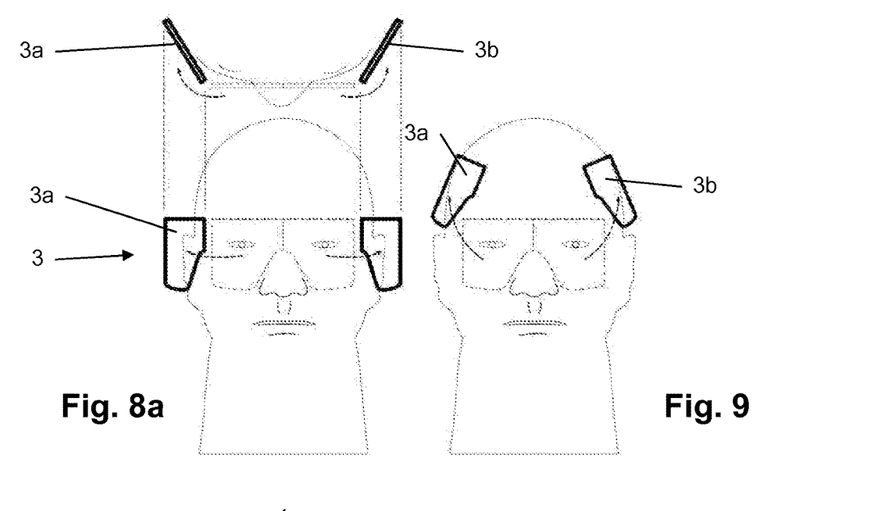
FIG. 8*a-d* an optical filter retracted by rotating and/or moving sideways.
FIG. 9 an optical filter retracted by rotating sideways and upwards.
Figure 8B:
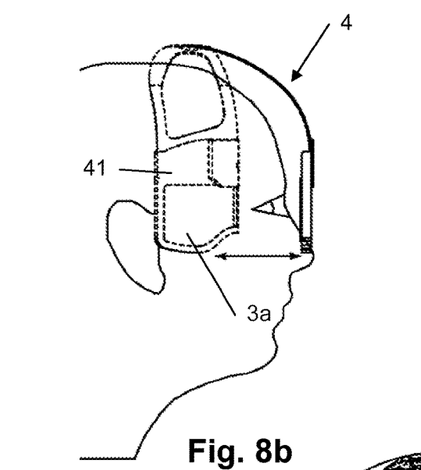
Figure 8C:
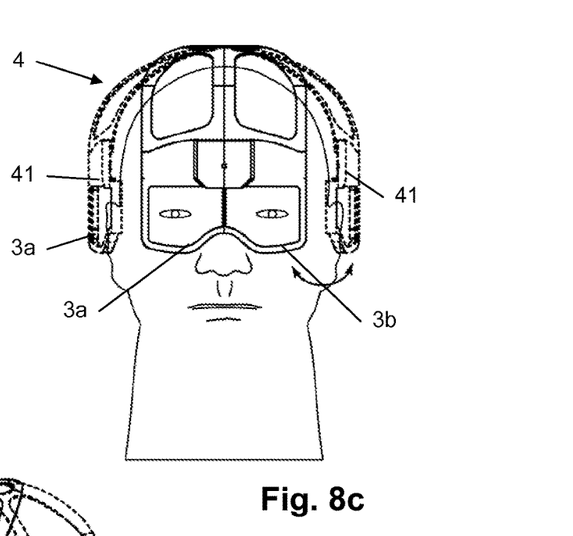
Figure 8D:
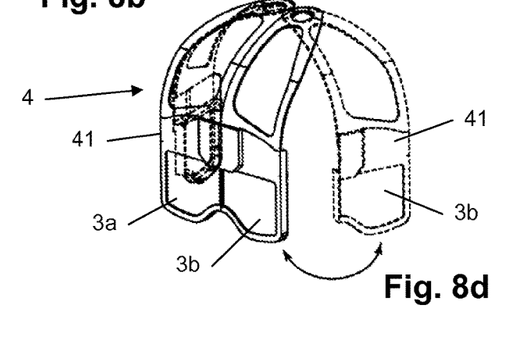

FIG. 8*a-d* show an optical filter 3 that is retracted by rotating and/or sliding the optical filter 3 sideways. In the embodiment of FIGS. 8*b*-8*d* the filter carrying element 41 comprises two separate sections, each carrying one of the separate sections 3*a*, 3*b* of the optical filter. The sections of the filter carrying element 41 are arranged to rotate around a substantially vertical axis.

FIG. 9 shows an optical filter 3 that is retracted by rotating sideways and upwards.

Figure 12:
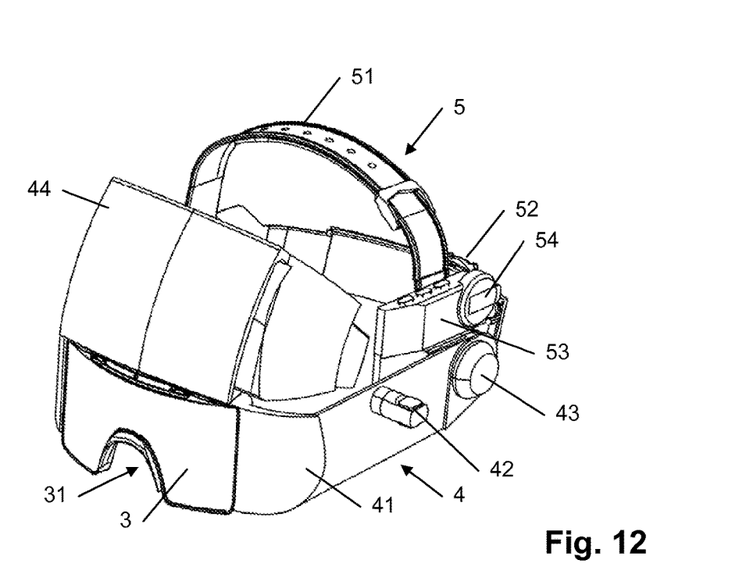
FIG. 12 a device with a bent optical filter.

In all embodiments, the optical filter 3 can be of a curved shape, using thin and bent glass panes. This is particularly useful in those embodiments in which the optical filter 3 is retracted along a curved path, as is possible in the embodiments of FIGS. 3-5, 6*a*, 6*b*, 8, 9. The optical filter 3 thus can comprise a curved or spherical liquid crystal shutter element. The liquid crystal shutter element can comprise thin sheets of glass or plastic. These sheets serve as substrates and electrodes for the liquid crystal elements. Such sheets can be bent (after having been manufactured as flat or planar sheets) or shaped to be curved or spherical (i.e. by being created in a curved or spherical form). They can have a thickness between 0.1 mm and 0.25 mm. They can be manufactured from Polycarbonate (PC) or PET (Polyethylene). FIG. 12 shows an embodiment with a curved optical filter 3. It is similar the embodiment of FIGS. 1 to 5 in all aspects, except for that the optical filter 3 is curved or bent. In consequence, the elements carrying or accommodating the optical filter are adapted. The overall size of the device can be reduced and/or the field-of-view increased, when compared to a device comprising a flat optical filter 3.

Figure 10:
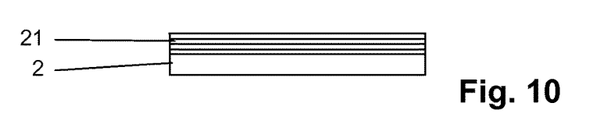
FIG. 10 a cross section through a front cover.

FIG. 10 shows a cross section through a part of the front cover 2, with a stack of sheets 21 that can be peeled off one after the other when the outermost sheet is damaged, revealing an undamaged underlying sheet and allowing for a clear view through the front cover 2. Details on the realization of such a stack of sheets are disclosed in e.g. patent application US 2004/258933.

Figure 11:
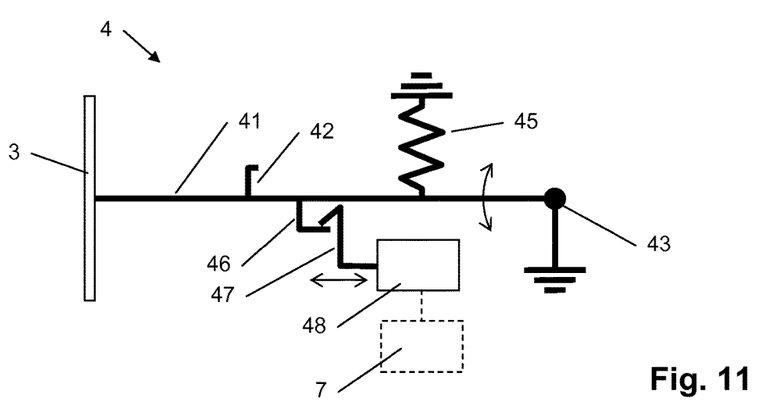
FIG. 11 a schematic representation of a retracting mechanism.

FIG. 11 shows a schematic representation of the retracting mechanism 4 and elements for activating the retracting mechanism 4. When activated, the retracting mechanism 4 moves the optical filter 3 from the active position to the retracted position. The retracting mechanism 4 comprises a spring 45 arranged to exert a force to move the filter carrying element 41 to the retracted position, and a releasable catch 46 arranged to hold the filter carrying element 41 in the active position. The catch 46 is held by a holding element 47. The holding element 47 can be moved by a manually moved element or by an actuator 48, typically an electromechanical actuator. In the latter case, a detection unit 7 is arranged to release the catch 46 in order to activate the retracting mechanism 4. This can be done by moving the catch 46 or the holding element 47 or both.

The actuator is driven or controlled by the detection unit 7, which detects when a welding operation has stopped and automatically activates the retracting mechanism 4. The detection unit 7 can be configured to be in an active mode or in a power saving sleep mode, wherein in the active mode the detection unit 7 detects when a welding operation has stopped and automatically activates the retracting mechanism 4, and wherein the detection unit 7 is automatically switched to be in the sleep mode when the optical filter 3 is in the retracted position. This allows for a power saving operation of the device. In the sleep mode, the detection unit 7 can be completely turned off, or it can automatically wake up at predetermined time intervals to check whether what position the optical filter 3 is in, and wake up in case that it is in the active position. The predetermined time intervals can be stored in the detection unit 7 or set by a user.

In another embodiment, the actuator 48 is a drive, such as an electrical motor, that directly drives a movement of the filter carrying element 41.

Throughout the present text, the terms such as upwards, down, sideways, vertical etc. relate to the position of the welder protecting device in an upright position, as on a wearer's upright head.

While the invention has been described in present embodiments, it is distinctly understood that the invention is not limited thereto, but may be otherwise variously embodied and practised within the scope of the claims.

The invention claimed is:

1. A welder protection device comprising
   a shell and a transparent front cover for protection of a wearer of the welder protection device, and
   an auto-darkening optical filter, wherein
   the welder protection device further comprises a retracting mechanism arranged to move the optical filter from an active position to a retracted position and vice versa, wherein the front cover is a clear protective front cover, wherein the optical filter moves within or behind the shell and the front cover of the welder protection device while the front cover and the shell remain in place, and wherein a motion of the retracting mechanism is swiveling motion around a hinge, wherein
   in the active position the optical filter lies within or behind the shell and the front cover of the welder protection device and in the wearer's field of view, and
   in the retracted position the optical filter lies within or behind the shell and the front cover of the welder protection device and outside the wearer's field of view.

2. The welder protecting device of claim 1, wherein the wearer's field of view is determined by an opening in the shell, the shell being opaque and the opening being covered by the transparent front cover, and
   when the optical filter is in the active position, the optical filter and a filter carrying element cover the opening,
   wherein, when the optical filter is in the retracted position, the optical filter is arranged adjacent to the opening, and the optical filter is arranged to not cover the opening or to not substantially cover the opening.

3. The welder protecting device of claim 2, wherein the optical filter comprises a concave cutout for accommodating a wearer's nose.

4. The welder protecting device of claim 2, wherein the optical filter comprises a curved or spherical liquid crystal shutter element.

5. The welder protecting device of claim 2, wherein in the active position, when the welder protecting device is worn by a wearer, the optical filter is distanced from the wearer's eyes by 20 mm to 40 mm.

6. The welder protection device of claim 2, comprising a detection unit configured to automatically activate the retracting mechanism to move the optical filter from the active position, wherein the retracting mechanism is held by a catch, to the retracted position, the catch is arranged to automatically release the retracting mechanism when the detection unit detects an end of a welding operation.

7. The welder protecting device of claim 2, wherein the retracting mechanism comprises a spring arranged to exert a force to move the filter carrying element to the retracted position, wherein
   the retracting mechanism is configured to be manually brought into the active position against a tension of the spring, and wherein
   the retracting mechanism further comprises a releasable catch arranged to hold the filter carrying element in the active position.

8. The welder protection device of claim 2, wherein the retracting mechanism moves the optical filter from the active to the retracted position along an arcuate path around a hinge, wherein
   a filter carrying element that holds the optical filter is adapted to rotate about the hinge, the hinge is attached to at least one of the shell and a support of the welder protection device.

9. The welder protection device of claim 1, wherein the optical filter comprises a concave cutout for accommodating a wearer's nose.

10. The welder protection device of claim 9, wherein the optical filter comprises a liquid crystal shutter element, the liquid crystal shutter element comprises thin sheets of glass or plastic which are bent or shaped to be curved or spherical and have a thickness between 0.1 mm and 0.25 mm.

11. The welder protecting device of claim 1, wherein the optical filter comprises a curved or spherical liquid crystal shutter element.

12. The welder protection device of claim 1, wherein in the active position, when the welder protecting device is worn by a wearer, the optical filter is distanced from the wearer's eyes by 20 mm to 40 mm.

13. The welder protection device of claim 1, comprising a detection unit configured to automatically activate the retracting mechanism to move the optical filter from the active position, where the retracting mechanism is held by a catch, to the retracted position, the catch is arranged to automatically release the retracting mechanism when the detection unit detects an end of a welding operation.

14. The welder protecting device of claim 13, wherein the detection unit is configured to be in an active mode or in a power saving sleep mode, wherein
in the active mode the detection unit detects when a welding operation has stopped and automatically activates the retracting mechanism, and wherein
the detection unit is automatically switched to be in the sleep mode when the optical filter is in the retracted position, and wherein
the detection unit wakes up from the sleep mode and is automatically switched to be in the active mode, when the optical filter is in the active position.

15. The welder protecting device of claim 1, wherein the retracting mechanism comprises a spring arranged to exert a force to move the filter carrying element to the retracted position, wherein
the retracting mechanism is further configured to be manually brought into the active position against a tension of the spring, and wherein
the retracting mechanism further comprises a releasable catch arranged to hold the filter carrying element in the active position.

16. The welder protecting device of claim 15, wherein the catch is held by a holding element which is moved by an actuator, and wherein
a detection unit is arranged to release the catch by the actuator in order to activate the retracting mechanism to move the optical filter from the active position to the retracted position.

17. The welder protection device of claim 1, wherein the retracting mechanism moves the optical filter from the active to the retracted position along an arcuate path around a hinge, wherein
a filter carrying element holding the optical filter is rotatable about the hinge, the hinge is attached to at least one of the shell and a support of the welder protection device.

18. The welder protection device of claim 1, wherein the optical filter comprises two separate sections which are movable relative to one another, and wherein
the retracting mechanism moves the separate sections of the optical filter from the active to the retracted position each along different translational and/or rotational trajectories.

19. The welder protection device of claim 1, wherein the front cover comprises a laminate comprising a stack of superimposed sheets each sheet adhering to an underlying sheet, wherein each sheet can be peeled off its underlying sheet.

* * * * *